US012676578B2

(12) United States Patent
Alzaher et al.

(10) Patent No.: US 12,676,578 B2
(45) Date of Patent: Jul. 7, 2026

(54) CURRENT-MODE SINUSOIDAL OSCILLATOR USING SINGLE CURRENT AMPLIFIER

(71) Applicant: KING FAHD UNIVERSITY OF PETROLEUM AND MINERALS, Dhahran (SA)

(72) Inventors: Hussain Abdullah Alzaher, Dhahran (SA); Ibrahim Mohammed Al Khalifa, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 248 days.

(21) Appl. No.: 18/657,172

(22) Filed: May 7, 2024

(65) Prior Publication Data

US 2025/0350241 A1      Nov. 13, 2025

(51) Int. Cl.
*H03B 5/20*      (2006.01)
*A61N 1/20*      (2006.01)

(52) U.S. Cl.
CPC    *H03B 5/20* (2013.01); *A61N 1/20* (2013.01)

(58) Field of Classification Search
CPC ................................... H03B 5/20; A61N 1/20
See application file for complete search history.

(56) References Cited

U.S. PATENT DOCUMENTS 8,482,351 B2 *    7/2013    Hou ...................... H03F 3/3001
                                                     330/255
9,503,098 B1    11/2016    Abuelma'atti et al.
2003/0137344 A1 *    7/2003    Kimball ................... H03F 1/34
                                                     330/9

FOREIGN PATENT DOCUMENTS

RU          2 697 945 C1      8/2019

OTHER PUBLICATIONS

Mancini; Design of op amp sine wave oscillators; Analog Applications Journal; Analog and Mixed-Signal Products; Aug. 2000; 5 Pages.

(Continued)

*Primary Examiner* — Jeffrey M Shin
(74) *Attorney, Agent, or Firm* — Oblon, McClelland, Maier & Neustadt, L.L.P.

(57)          ABSTRACT
A current mode sinusoidal oscillator includes a current amplifier with distinct current input and four output terminals. The amplifier includes a current input terminal X, a first and a second negative current feedback terminals $I_{fo1}$ and $I_{fo2}$, along with a positive current output terminal $I_{op}$ and a negative current output terminal $I_{on}$. The oscillator is characterized by a first feedback path that transmits a portion of a current at the first negative current feedback terminal $I_{fo1}$ to the current input terminal X of the oscillator. Additionally, a second feedback path, interlinking $I_{fo2}$ and X, comprises a three-stage phase lag network designed to confer a phase shift of negative 180 degrees to the current signal at a frequency of oscillation determined by capacitor and resistor values of the three-stage phase lag network. A load is connected between $I_{op}$ and $I_{on}$, which receives the sinusoidal current at the frequency of oscillation.

20 Claims, 6 Drawing Sheets

(56) References Cited

OTHER PUBLICATIONS

Ee-diary; LM741 phase shift oscillator design; ee-diary.com/2023/04/lm741-phase-shift-oscillator-design.html; Apr. 1, 2023.

Analog Devices; 60 MHz, 2000 V/µs, Monolithic Op Amp with Quad Low Noise; AD844 Data Sheet; 2017; 20 Pages.

National Semiconductor; LM158/LM258/LM358/LM2904 Low Power Dual Operational Amplifiers; Nov. 2000; 24 Pages.

Alzaher; Novel Schmitt trigger and square-wave generator using single current amplifier; IEEEAccess; 2017; 8 Pages.

* cited by examiner

Pin 1

CURRENT-MODE SINUSOIDAL OSCILLATOR USING SINGLE CURRENT AMPLIFIER

BACKGROUND

Technical Field

The present disclosure is directed to the field of signal processing systems, more particularly to current mode sinusoidal oscillators (SOs) using a four output current amplifier.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In electronic systems, oscillators are utilized in various applications ranging from communications to biomedical and power management circuits. Oscillators are instrumental in executing various functions, such as timing, controlling switches, modulating and demodulating carrier signals, decomposing signals, and stimulating bioimpedance.

Various configurations of oscillators have been developed over the years, among those, square wave oscillators are the predominant choice in many applications. The preference for square wave oscillators is primarily due to their capability for wide-range tuning and their proficiency in maintaining an accurate amplitude. Additionally, the majority of oscillators are configured in a voltage-mode configuration. The voltage-mode configurations are extensively used for generating carrier signals in communication circuits and serving as a test signal for characterizing various circuits. The fundamental limitation of the voltage mode configuration is its reliance on voltage signals, necessitating the inclusion of an additional circuitry for voltage-to-current (V/I) conversion. This requirement increases the complexity of the system and also requires increased area and power consumption.

Therefore, current-mode sinusoidal oscillators are preferred in specific applications, particularly where safety concerns necessitate the use of fully differential (FD) current signals. A few such critical applications are as current drivers for electrical impedance spectroscopy (EIS) and electrical impedance tomography (EIT) and similar fields, particularly biomedical applications, where the harmonic purity of sinusoidal oscillators is indispensable. In addition to biomedical applications, charge-controlled MEMs-elements, which are components exhibiting memory-dependent behavior, require a sinusoidal current input. The sinusoidal current input is necessary to measure characteristics, such as the pinched hysteresis loop (PHL) of these devices.

Over the years, various designs of current-mode sinusoidal oscillators have been developed. The designs include oscillators built using current-controlled current follower transconductance amplifiers (CCFTA), multiplication mode current conveyors (MMCC), current differencing buffered amplifiers (CDBA), multifunction current differencing cascaded transconductance amplifiers (MCDCTA), and the like. These designs typically aim to fulfill basic requirements of sinusoidal oscillators, such as independent tuning of the condition of oscillation (CO) and the frequency of oscillation (FO), while also providing additional functionalities such as tunability and filtering using the same circuit.

In conventional technology, a current driver has been designed using look up tables (LUT), filters, clocks, and a V/I converter to obtain a pseudo sinusoidal waveform. Since the sine wave generated from LUT has high harmonic content, $g_m$—C filters were used to reject harmonics. A V/I converter which includes a low drop out (LDO) converter was used. In an alternate solution, a Wein-bridge based sinusoidal oscillator was used; thus, both clocks and LUT were avoided. Since the signal naturally has low harmonic content, the filters are also not needed. However, since the oscillator used generates a voltage signal, a V/I converter is required.

While current-mode outputs are provided in these designs, the active elements employed are not purely current-mode. This introduces voltage-mode limitations such as limited voltage swings due to power supply constraints, issues with common-mode feedback (CMFB) in fully differential implementations, and restricted input common-mode range (ICMR).

Patent application RU2697945C1 describes an active RC low-pass filter of the third order based on an operational amplifier with a para-phase output which contains a differential operational amplifier with inverting and non-inverting antiphase outputs, resistors, capacitors. However, this patent does not describe an oscillator and operates in a voltage-mode.

U.S. Pat. No. 9,503,098B1 describes a current-feedback operational amplifier-based sinusoidal oscillator circuit including a pair of CFOAs connected to each other using five resistors and two capacitors. However, this circuit includes two active elements, provides only a single ended output and the circuit configuration is not similar to the circuit of the present disclosure.

Non-patent publication "LM741 *phase shift oscillator design*" describes an LM741 operational amplifier used in phase shift oscillator circuit. The LM741 op amp oscillator circuit used inductors and capacitors as feedback network. However, this publication operates in voltage mode, has only a single ended output and does not output current signals in a differential mode.

The aforementioned disclosures fail to an oscillator operating in current mode and having differential outputs, which use current amplifiers (CAs) and which offers stability, improved common-mode rejection, controlled gain, reduced distortion and effective signal isolation.

Each of the aforementioned disclosures suffers from one or more drawbacks hindering their adoption. Accordingly, it is one object of the present disclosure to provide a current-mode sinusoidal oscillator with differential outputs which outputs sinusoidal current signals.

SUMMARY

In an exemplary embodiment, a current mode sinusoidal oscillator is described. The sinusoidal oscillator includes a current amplifier having a current input terminal X, a first negative current feedback terminal $I_{fo1}$, a second negative current feedback terminal $I_{fo2}$, a positive current output terminal $I_{op}$ and a negative current output terminal $I_{on}$, a first feedback path connected between the first negative current feedback terminal $I_{fo1}$ and the input terminal x, wherein the first feedback path is configured to transmit a portion of a current at the first negative current feedback terminal $I_{fo1}$ to the current input terminal X, a second feedback path connected between the second negative current feedback terminal $I_{fo2}$ and the current input terminal X, wherein the second feedback path is a three stage phase lag network configured to shift the phase of the current in the second feedback path by a negative 180 degrees with respect to the input current at a frequency of oscillation, and a load connected between the positive current output terminal $I_{op}$ and the negative current output terminal $I_{on}$, wherein an output current through the load is sinusoidal.

In another exemplary embodiment, a current driver for biomedical stimulation is described. The current driver includes a current source, a switch connected to the current source, wherein the switch is configured to one of connect and disconnect the current, a current amplifier having a current input terminal X connected to the switch, a first negative current feedback terminal $I_{fo1}$, a second negative current feedback terminal $I_{fo2}$, a positive current output terminal $I_{op}$ and a negative current output terminal $I_{on}$, a first feedback path connected between the negative current feedback terminal $I_{fo1}$ and the input terminal X, wherein the first feedback path is configured to transmit a portion of a current at the first negative current feedback terminal $I_{fo1}$ to the current input terminal X, a second feedback path connected between the second negative current feedback terminal $I_{fo2}$ and the current input terminal X, wherein the second feedback path is a three stage phase lag network configured to shift the phase of the current in the second feedback path by a negative 180 degrees at a frequency of oscillation with respect to the input current, and a biomedical stimulator connected between the positive current output terminal $I_{op}$ and the negative current output terminal $I_{on}$, wherein an output current driven through the biomedical stimulator is sinusoidal.

In another exemplary embodiment, a method for providing biomedical stimulation is described. The method includes connecting a current source to an input terminal of a current mode sinusoidal oscillator, switching, by a switch connected to the current source, the current source to ON, wherein the current mode sinusoidal oscillator includes a current amplifier having a current input terminal x connected to the switch, a first negative current feedback terminal $I_{fo1}$, a second negative current feedback terminal $I_{fo2}$, a positive current output terminal $I_{op}$ and a negative current output terminal $I_{on}$, connecting a first feedback path between the first negative current feedback terminal $I_{fo1}$ and the input terminal X, wherein the first feedback path is configured to transmit a portion of a current at the first negative current feedback terminal $I_{fo1}$ to the current input terminal X, connecting a second feedback path between the second negative current feedback terminal $I_{fo2}$ and the input terminal X, wherein the second feedback path is a three stage phase lag network configured to shift the phase of a current in the second feedback path by a negative 180 degrees at a frequency of oscillation with respect to the input current, connecting a biomedical load between the positive current output terminal $I_{op}$ and the negative current output terminal $I_{on}$, and driving a sinusoidal output current through the biomedical load.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
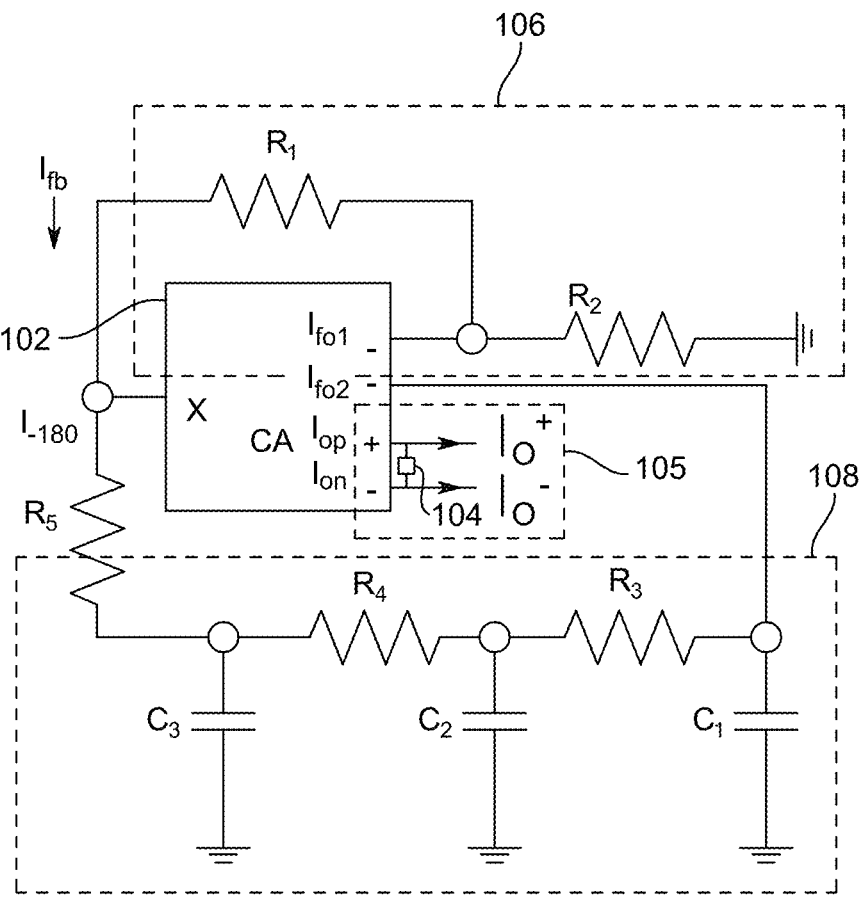
FIG. 1 illustrates a schematic of a current-mode sinusoidal oscillator, according to certain embodiments.

In the drawings, like reference numerals designate identical or corresponding parts throughout the several views. Further, as used herein, the words "a", "an" and the like generally carry a meaning of "one or more", unless stated otherwise.

Furthermore, the terms "approximately". "approximate", "about" and similar terms generally refer to ranges that include the identified value within a margin of 20%, 10%, or preferably 5%, and any values therebetween.

Aspects of this disclosure are directed to a system, device, and method for the configuration of a current mode sinusoidal oscillator. The current mode sinusoidal oscillator is implemented through a current amplifier equipped with a unique arrangement of feedback paths that manipulate the phase of current signals to achieve sinusoidal oscillation. The configuration is adept at maintaining the integrity of the sinusoidal waveform through the load connected between differential output terminals of the amplifier. The current mode sinusoidal oscillator renders improved signal stability and reduced sensitivity to component variations, which are common challenges in traditional voltage mode oscillators. Additionally, the current mode approach offers inherent benefits in terms of power efficiency and the potential for miniaturization, making it suitable for integrated circuit applications where space and power consumption are important. The current mode sinusoidal oscillator is preferably used as a current driver for electrical impedance in, but not limited to, spectroscopy, tomography and biomedical applications.

FIG. 1 illustrates the circuit of a current amplifier (CA) based phase-shift oscillator having four output terminals. The oscillator includes a current amplifier (CA) 102, a first feedback path 106, a second feedback path 108 formed by an RC network, and a load 104 which receives the sinusoidal output current at its terminals $O^+$ and $O^-$.

The CA is configured with a current input terminal designated X, a first negative current feedback terminal $I_{fo1}$, a second negative current feedback terminal $I_{fo2}$, along with a positive current output terminal $I_{op}$, and a negative current output terminal $I_{on}$.

The first feedback path 106 connects the first negative current feedback terminal $I_{fo1}$ to the current input terminal X. This negative feedback path sets the closed loop gain of the CA such that $$\frac{I_{fo2}}{I_{-180}} = -\left(1 + \frac{R_1}{R_2}\right).$$

The first feedback path 106 is composed of a first leg and a second leg. The first leg includes a first resistor $R_1$ positioned between the first negative current feedback terminal $I_{fo1}$ and the current input terminal X. The second leg includes a second resistor $R_2$ that connects the first negative current feedback terminal $I_{fo1}$ to a ground terminal. These resistors are crucial in defining the current division and hence in determining the gain characteristics of the oscillator.

In an illustrative implementation, the resistor $R_1$ possesses a value of approximately 32 kΩ, and resistor $R_2$ has a value of approximately 1 kΩ.

A second feedback path 108 extends from the second negative current feedback terminal $I_{fo2}$ to the current input terminal X. The second feedback path 108 is a three-stage phase lag RC network which is configured to result in a phase shift of the current by negative 180 degrees relative to the phase of the input current. The phase shift is desired for achieving the sinusoidal oscillation required by the circuit. RC networks are typically used to obtain the desired phase shift in the oscillator to convert a negative feedback loop into a positive feedback loop at one frequency. In general, the RC networks can have a high pass (HP) or low pass (LP) magnitude frequency response. LP RC networks provide a negative phase shift, whereas HP RC networks provide a positive phase shift. Without loss of generality, the circuit of the present disclosure will focus on low pass RC networks.

The second feedback path 108 is formed by a series arrangement of a third resistor $R_3$, a fourth resistor $R_4$, and a fifth resistor $R_5$, culminating at the input terminal X. A set of capacitors is connected within the resistor series, where a first capacitor $C_1$ connects one terminal to the second negative current feedback terminal $I_{fo2}$ and its other terminal to the ground. A second capacitor $C_2$ is connected at its first terminal to the junction between the third resistor $R_3$ and the fourth resistor $R_4$, with its second terminal also grounded. A third capacitor $C_3$ is similarly connected at its first terminal to the junction between the fourth resistor $R_4$ and the fifth resistor $R_5$ with its other terminal grounded. This capacitor array forms a phase lag network in the oscillator circuit.

The operational parameters of the oscillator, that is, the frequency of oscillation (FO) and the condition of oscillation (CO), are predicated upon the relationships among the feedback network components, using equations (1) and (2):

$$FO: f_o = \frac{\sqrt{6}}{2\pi RC}, \quad (1)$$

where R represents the resistance values of $R_3$, $R_4$, and $R_5$, and C denotes the capacitance values of $C_1$, $C_2$, and $C_3$. The selection of these component values is in alignment with the requisite oscillation conditions and frequency. In a non-limiting example, the resistors $R_3$, $R_4$, and $R_5$ are each about 2 KΩ, and the capacitors $C_1$, $C_2$, and $C_3$ each have a capacitance of approximately 10 nF. These component values are selected to enable the desired oscillation conditions and frequency. The condition of oscillation (CO) is given by:

$$CO:\left(1 + \frac{R_1}{R_2}\right) = 29, \quad (2)$$

In practice the gain should be slightly larger so the oscillation will grow in amplitude.

The CA 102 is further configured with a positive current output terminal ($I_{op}$) and a negative current output terminal ($I_{on}$). In the operation of a current amplifier, especially one configured as a current-feedback operational amplifier (CFOA), the $I_{op}$ and $I_{on}$ terminals are implemented where the amplified output current is available. The $I_{op}$ sources the current, while $I_{on}$ sinks the current. In an ideal current amplifier, the currents at these terminals are equal in magnitude but opposite in direction, adhering to the equation:

$$I_{op} = -I_{on},$$

where the current gain ($A_i$) tends towards infinity.

In the oscillator circuit, a load 104 is connected between the two output terminals ($I_{op}$ and $I_{on}$), and the sinusoidal current that oscillates through this load 104 is the output 105 of the oscillator. The configuration ensures that the current flowing through the load 104 is sinusoidal. The characteristics of the output of this current, including its amplitude and frequency, are determined by the various components and feedback paths.

Figure 2:
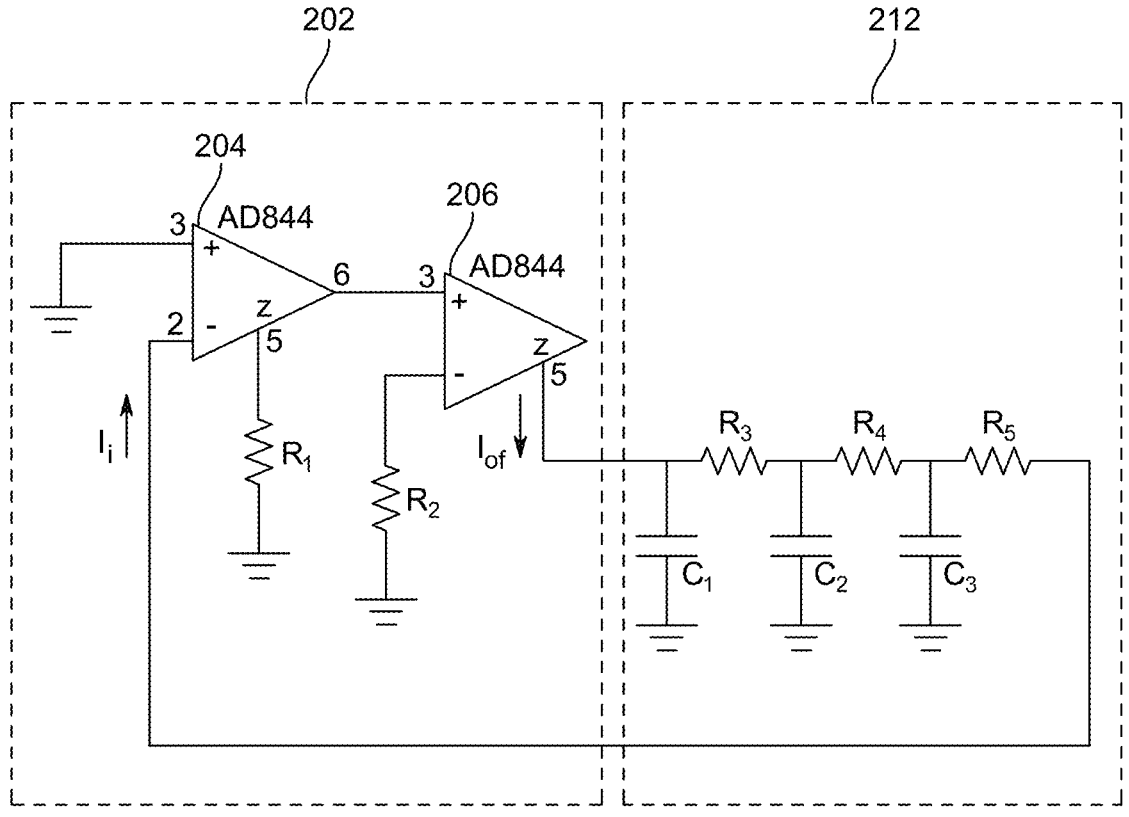
FIG. 2 illustrates a prototype circuit of a current-mode sinusoidal oscillator, according to certain embodiments.

FIG. 2 illustrates a schematic of a prototype circuit of a current-mode sinusoidal oscillator which is used to verify the operation of the current amplifier (CA) based phase-shift oscillator of the present disclosure which is shown in FIG. 1. The prototype circuit is implemented using off-the-shelf integrated circuits. The current-mode sinusoidal oscillator, referred to as an oscillator hereinafter, is configured to deliver accurate sinusoidal current output.

As shown in FIG. 2, CA 102 is configured using two operational amplifiers and a phase lag feedback path 212. The two operational amplifiers are depicted as a first amplifier 204 and a second amplifier 206. The combination of the two amplifiers provides the CA 102 with a negative gain output −K, where K=$R_1$/$R_2$. The feedback passive network is same in both figures (FIG. 1 and FIG. 2).

The first amplifier 204 is configured as a current-feedback operational amplifier. In a non-limiting example, the first amplifier 204 and the second amplifier 206 are implemented by an AD844 monolithic op amp, manufactured by Analog Devices, Norwood, Massachusetts, United States of America. The op amp is optimized for current to voltage (I/V) application while in an inverting mode. The non-inverting input terminal (+), pin 3 of the first amplifier 204, is connected to a ground terminal. The inverting input terminal (−), pin 2, is fed with a feedback current signal generated through the phase-lag feedback path 212.

In FIG. 2, an input current $I_i$ at terminal 2 of the first amplifier 204 generates a voltage at terminal 5 of 204 equal to −$R_1$$I_i$. This voltage appears as −$R_1$$I_i$, at the non-inverting terminal 3 of the second amplifier 206, which generates a current equal to $R_1$$I_i$/$R_2$ at the inverting input terminal (−) (pin 2 of the second AD844). Consequently, an equal current is generated at the output terminal 5 (pin Z) so that $I_{of}$=−$R_1$$I_i$/$R_2$.

The output of the second amplifier 206 is then fed to a second feedback path 212 including a three-stage resistor-capacitor (RC) phase lag network. The RC network includes a series connection of resistors, referred to as a third resistor $R_3$, a fourth resistor $R_4$, and a fifth resistor $R_6$, which are connected between the output terminal z (pin 5) of the second amplifier 206 and the inverting input terminal (pin 2) of the first amplifier 204. In a non-limiting example, each of the third, fourth and fifth resistors has a value of approximately 2 KΩ.

A set of capacitors, referred to as a first capacitor $C_1$, a second capacitor $C_2$, and a third capacitor $C_3$, is connected in parallel to the series resistors. The capacitors provide the essential phase shift required for oscillation by being connected to corresponding resistors and to a common ground, thereby collectively contributing an overall phase shift of negative 180 degrees required for oscillation. In a non-limiting example, each capacitor $C_1$, $C_2$ and $C_3$ has a capacitance of 10 nF.

The three-stage RC network 212 is composed of the three resistors and the three capacitors, each of which create an additional phase shift. Each resistor is paired with a capacitor in parallel, with one terminal connected to the output terminal of the second amplifier 206, and the other terminal grounded. The phase lag feedback path is implemented for the stabilization of the oscillation frequency and the enforcement of the condition of oscillation, ultimately ensuring the generation of a consistent sinusoidal output.

The output of the last resistor $R_5$ is fed back to the inverting input (pin 2) of the first amplifier 204, rendering the oscillation configuration as a closed feedback loop.

The output of the prototype current amplifier (CA) based phase-shift oscillator shown in FIG. 2 is taken across the resistor $R_2$.

In an exemplary embodiment, a current driver for biomedical stimulation is implemented. The current driver includes a current source, a switch connected to the current source, where the switch is configured to one of connect and disconnect the current, and the current-mode sinusoidal oscillator as described with reference to FIG. 1.

In another exemplary embodiment, method for providing biomedical stimulation is disclosed. The method includes connecting a current source to an input terminal of a current mode sinusoidal oscillator, switching, by a switch connected to the current source, the current source ON, where the current mode sinusoidal oscillator includes a current amplifier having a current input terminal x connected to the switch, a first negative current feedback terminal Ifo, a second negative current feedback terminal $I_{fo2}$, a positive current output terminal $I_{fo1}$, and a negative current output terminal $I_{on}$, connecting a first feedback path 206 between the first negative current feedback terminal $I_{fo1}$ and the input terminal x, where the first feedback path 206 is configured to provide a negative feedback current in the first feedback path 206 which adds to the input current, connecting a second feedback path 208 between the second negative current feedback terminal $I_{fo2}$ and the input terminal x, where the second feedback path 208 is a three stage phase lag network configured to shift the phase of the current in the second feedback path 208 by a negative 180 degrees with respect to the input current, connecting a biomedical load 204 between the positive current output terminal $I_{op}$ and the negative current output terminal $I_{on}$; and driving a sinusoidal output current through the biomedical load 204.

Figure 3A:
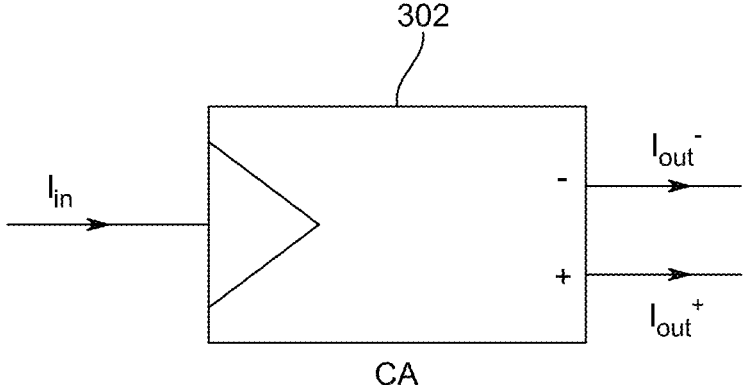
FIG. 3A depicts a circuit symbol of a differential output current amplifier (CA), according to certain embodiments.

FIG. 3A depicts a circuit symbol of a current amplifier (CA). The CA 202 symbol represents the current input and output terminals, providing a standardized depiction used for circuit diagrams and design schematics. The symbol is recognized in the field of electronics and is essential for conveying the function and connectivity of the CA 202 within a circuit.

Figure 3B:
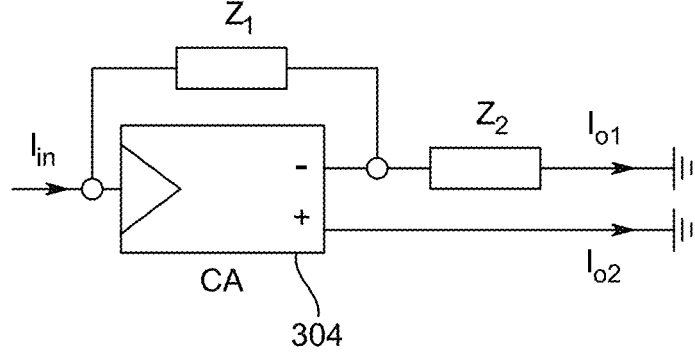
FIG. 3B depicts a generalized closed loop amplifier using a single CA, according to certain embodiments.

FIG. 3B depicts a generalized CA circuit. The CA can be configured in two configurations. First, an open-loop, and second, a negative feedback loop. The configuration is determined by the desired characteristics of the circuit.

In the open-loop configuration, the gain $(A_i)$ of the CA is designed to be finite. Finite gain is achieved by utilizing the gain inherent to a current mirror, allowing for a specific and stable amplification factor. However, in a negative feedback configuration, the gain $(A_i)$ is theoretically infinite. FIG. 3B depicts a generalized model which may be configured such that the current gain is so large that it approaches infinity. The CA is defined to have a singular input terminal for current input ($I_{in}$), and two output terminals that provide differential output terminals $I_{o1}$ and $I_{o2}$.

The closed loop amplifier of FIG. 3B has a gain given by $$\frac{I_{o2}}{I_{in}} = \left(1 + \frac{R_1}{R_2}\right).$$

An inverting gain is obtained if a negative output terminal instead of the positive output terminal is used to provide $I_{o2}$ as shown in the oscillator of FIG. 1 wherein $$\frac{I_{fo2}}{I_{-180}} = -\left(1 + \frac{R_1}{R_2}\right).$$

The versatility of the CA is further emphasized by its ability to realize a variety of op-amp circuits. When a CA is placed in a closed-loop configuration with two generalized impedances, it can function as a buffer, integrator, differentiator, inverting amplifier, or non-inverting amplifier. The implementation of such functions is achieved by appropriately choosing and connecting the generalized impedances in the feedback path and the input path of the CA.

In an example, an inverting amplifier configuration is obtained when the CA is connected with a feedback impedance and an input impedance in such a manner that the output current is an inverted and scaled version of the input current. Similarly, a non-inverting amplifier is realized when the input is fed through a non-inverting terminal and the feedback network is arranged to maintain the phase of the output current in alignment with the input current, while still providing the desired gain.

Figure 4:
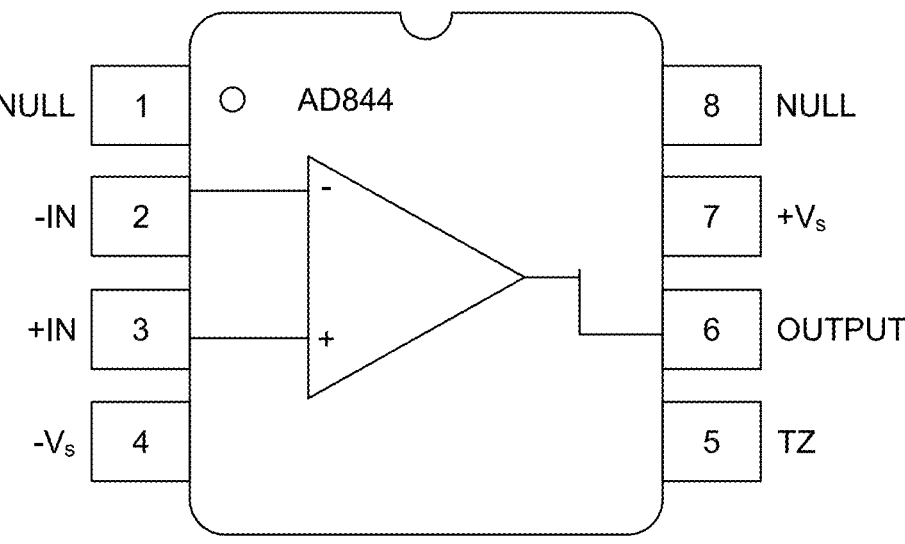
FIG. 4 illustrates a schematic of an AD844 Integrated Circuit (IC) pin configuration, according to certain embodiments.

FIG. 4 illustrates a schematic of an AD844 Integrated Circuit (IC) pin configuration, which is representative of the AD844 amplifiers 204 and 206 used in the prototype circuit of FIG. 2.

Pin 1: Null input.

Pin 2: Inverting input.

Pin 3: Non-inverting input.

Pin 4: Negative bias voltage input, which is necessary to operate an amplifier.

Pin 5: TZ current output terminal, which is an internal pre-buffered output.

Pin 6: Output.

Pin 7: Positive bias voltage input.

Pin 8: Null.

Figure 5:
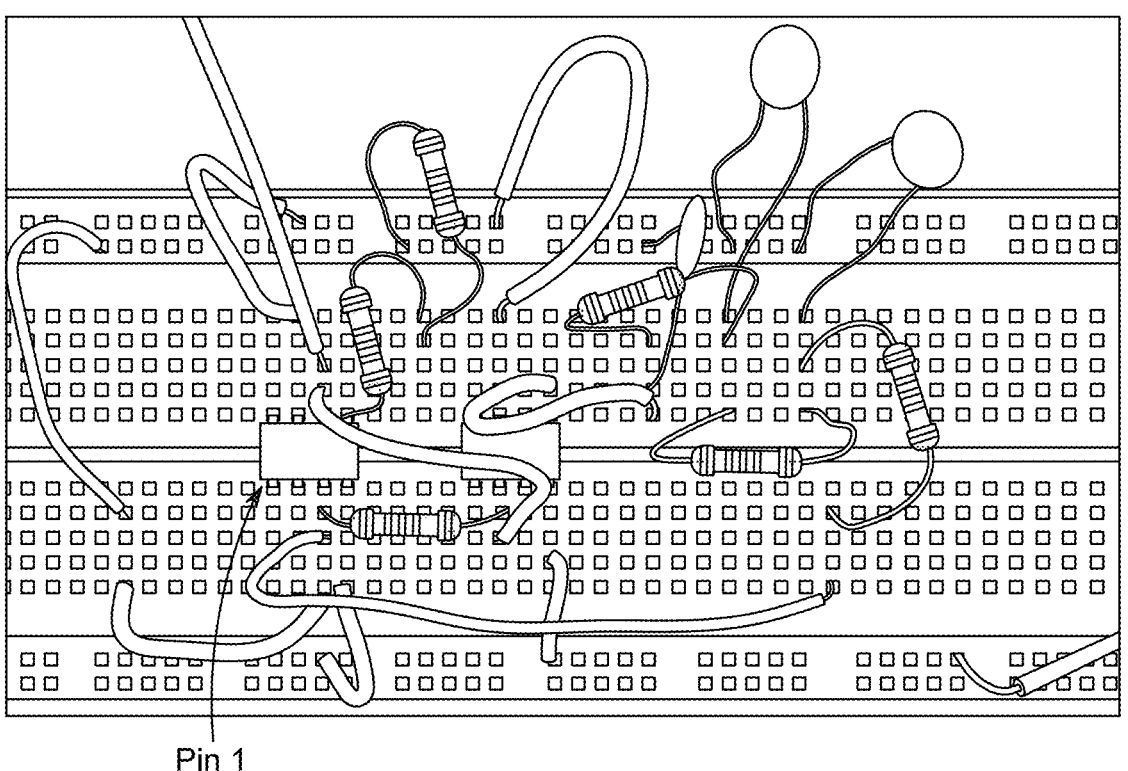
FIG. 5 illustrates the layout of a prototype of the current-mode sinusoidal oscillator implemented on a breadboard, according to certain embodiments.

FIG. 5 illustrates the layout of the prototype of the current-mode sinusoidal oscillator of FIG. 2 implemented on a breadboard. In FIG. 5, $R_2$ is connected between pin 2 of the second amplifier 206 and pin 3 of the load 204 which is connected to ground. $R_1$ is formed by two series resistors connected between pin 5 of the load 204 and ground.

Figure 6:
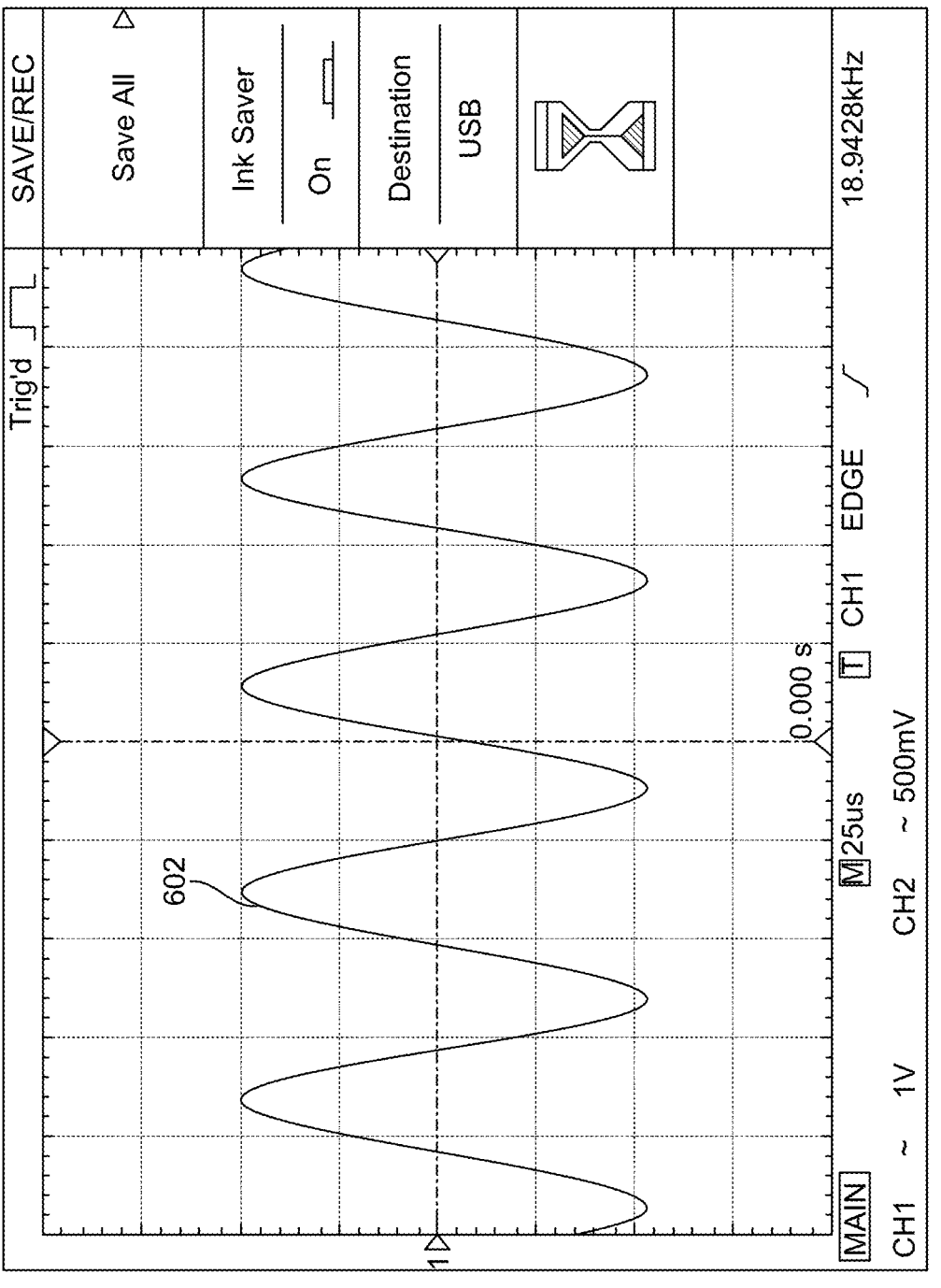
FIG. 6 is a graph of a sinusoidal wave generated by a current-mode sinusoidal oscillator, according to certain embodiments.

FIG. 6 represents a sinusoidal wave generated by the current mode sinusoidal oscillator. Graph 602 indicates an output sinusoidal waveform generated by the oscillator, proving the viability of the oscillator. The oscillator was configured with specific parameter values. Resistor and capacitor values: $R_1=32$ KΩ, $R_2=1$ KΩ, R=2 KΩ, and C=10 nF. The configuration of these components within the circuit is meant to produce a certain frequency of oscillation (FO). The result shown in the figure likely demonstrates the actual performance of the oscillator, which may slightly differ from the theoretical predictions due to real-world factors such as the tolerance of passive components and the parasitic effects that can occur on a breadboard.

The experimental results of FIG. 6 generated by the prototype circuit of the current-mode sinusoidal oscillator demonstrate a measured frequency of oscillation is approximately 18.9 kHz compared to the ideal frequency 19.5 kHz that represents a 3% error. The error between the experimental results and the thoracically calculations is due to the inaccuracy of the passive components, non-ideal terminal characteristics of the AD844, stray capacitances associated with breadboard implementation.

Embodiments are illustrated with respect to FIG. 1 to FIG. 9. In an exemplary embodiment, a current mode sinusoidal oscillator is described. The sinusoidal oscillator includes a current amplifier having a current input terminal X, a first negative current feedback terminal $I_{fo1}$, a second negative current feedback terminal $I_{fo2}$, a positive current output terminal $I_{op}$ and a negative current output terminal $I_{on}$, a first feedback path connected between the first negative current feedback terminal $I_{fo1}$ and the input terminal X, transmit a portion of a current at the first negative current feedback terminal $I_{fo1}$ to the current input terminal X, a second feedback path connected between the second negative current feedback terminal $I_{fo2}$ and the input terminal X, wherein the second feedback path is a three stage phase lag network configured to shift the phase of the current in the second feedback path by a negative 180 degrees with respect to the input current at a frequency of oscillation, and a load connected between the positive current output terminal $I_{op}$ and the negative current output terminal $I_{on}$, wherein an output current through the load is sinusoidal.

In an aspect, the first feedback path includes a first leg including a first resistor $R_1$ connected between the first negative current feedback terminal $I_{fo1}$ and the current input terminal x, and a second leg comprising a second resistor $R_2$ connected between the first negative current feedback terminal $I_{fo1}$ and a ground terminal.

In an aspect, the second feedback path includes a third resistor $R_3$ connected to the second negative current feedback terminal $I_{fo2}$, a fourth resistor $R_4$ connected in series with the third resistor $R_3$, a fifth resistor $R_5$ connected in series with the fourth resistor $R_4$, wherein the fifth resistor $R_5$ is connected to the input terminal X, a first capacitor $C_1$ having a first terminal connected to the second negative current feedback terminal $I_{fo2}$ and a second terminal connected to the ground terminal, a second capacitor $C_2$ having a first terminal connected to a junction between the third resistor $R_3$ and the fourth resistor $R_4$ and having a second terminal connected to the ground terminal, and a third capacitor $C_3$ having a first terminal connected to a junction between the fourth resistor $R_3$ and the fifth resistor $R_4$ and having a second terminal connected to the ground terminal.

In an aspect, a condition of oscillation (CO) of the output current is given by:

$$\left(1 + \frac{R_1}{R_2}\right) = 29.$$

In an aspect, a frequency of oscillation $f_0$ of the output current is given by:

$$f_o = \frac{\sqrt{6}}{2\pi RC},$$

where $R=R_3=R_4=R_5$ and $C=C_1=C_2=C_3$.

In an aspect, the resistor $R_1$ is about 32 kΩ, the resistor $R_2$ is about 1 kΩ, R is about 2 kΩ and C is about 10 nF.

In an aspect, the load is a biomedical stimulation device. The biomedical stimulation device may be selected from the group comprising a nerve stimulator, an electrode stimulator, a defibrillator, a deep brain stimulator, a muscle stimulator and the like.

In an aspect, the load is a power management load. The current mode sinusoidal current driver may be used to inject current into a circuit connected to the power management load to balance power or to correct power disturbances on power lines.

In another exemplary embodiment, a current driver for biomedical stimulation is described. The current driver includes a current source, a switch connected to the current source, wherein the switch is configured to one of connect and disconnect the current, a current amplifier having a current input terminal X connected to the switch, a first negative current feedback terminal $I_{fo1}$, a second negative current feedback terminal $I_{fo2}$, a positive current output terminal $I_{op}$ and a negative current output terminal $I_{on}$, a first feedback path connected between the negative current feedback terminal $I_{fo1}$ and the input terminal X, wherein the first feedback path is configured to transmit a portion of a current at the first negative current feedback terminal $I_{fo1}$ to the current input terminal X, a second feedback path connected between the second negative current feedback terminal $I_{fo2}$ and the current input terminal X, wherein the second feedback path is a three stage phase lag network configured to shift the phase of the current in the second feedback path by a negative 180 degrees at a frequency of oscillation with respect to the input current, and a load connected between the positive current output terminal $I_{op}$ and the negative current output terminal $I_{on}$, wherein an output current driven through the load is sinusoidal.

In an aspect, the first feedback path includes a first leg including a first resistor $R_1$ connected between the first negative current feedback terminal $I_{fo1}$ and the current input terminal x, and a second leg comprising a second resistor $R_2$ connected between the first negative current feedback terminal $I_{fo1}$ and a ground terminal.

In an aspect, the second feedback path includes a third resistor $R_3$ connected to the second negative current feedback terminal $I_{fo2}$, a fourth resistor $R_4$ connected in series with the third resistor $R_3$, a fifth resistor $R_5$ connected in series with the fourth resistor $R_4$, wherein the fifth resistor $R_5$ is connected to the input terminal X, a first capacitor $C_1$ having a first terminal connected to the second negative current feedback terminal $I_{fo2}$ and having a second terminal connected to the ground terminal, a second capacitor $C_2$ having a first terminal connected to a junction between the third resistor $R_3$ and the fourth resistor $R_4$ and having a second terminal connected to the ground terminal, and a third capacitor $C_3$ having a first terminal connected to a junction between the fourth resistor $R_3$ and the fifth resistor $R_4$ and having a second terminal connected to the ground terminal.

In an aspect, a condition of oscillation (CO) of the output current is given by:

$$\left(1 + \frac{R_1}{R_2}\right) = 29.$$

In an aspect, a frequency of oscillation $f_0$ of the output current is given by:

$$f_o = \frac{\sqrt{6}}{2\pi RC},$$

where $R=R_3=R_4=R_5$ and $C=C_1=C_2=C_3$.

In an aspect, the resistor $R_1$ is about 32 kΩ, the resistor $R_2$ is about 1 kΩ, R is about 2 kΩ and C is about 10 nF.

In an aspect, the biomedical load is selected from the group comprising a nerve stimulator, an electrode stimulator, a defibrillator, a deep brain stimulator and a muscle stimulator.

In another exemplary embodiment, a method for providing biomedical stimulation is described. The method includes connecting a current source to an input terminal of a current mode sinusoidal oscillator, switching, by a switch connected to the current source, the current source to ON, wherein the current mode sinusoidal oscillator includes a current amplifier having a current input terminal x connected to the switch, a first negative current feedback terminal $I_{fo1}$, a second negative current feedback terminal $I_{fo2}$, a positive current output terminal $I_{op}$ and a negative current output terminal $I_{on}$, connecting a first feedback path between the first negative current feedback terminal $I_{fo1}$ and the input terminal X, wherein the first feedback path is configured to transmit a portion of a current at the first negative current feedback terminal $I_{fo1}$ to the current input terminal X, connecting a second feedback path between the second negative current feedback terminal $I_{fo2}$ and the input terminal X, wherein the second feedback path is a three stage phase lag network configured to shift a phase of a current in the second feedback path by a negative 180 degrees at a frequency of oscillation with respect to the input current, connecting a biomedical load between the positive current output terminal $I_{op}$ and the negative current output terminal $I_{on}$, and driving a sinusoidal output current through the biomedical load.

In an aspect, connecting the first feedback path includes connecting a first leg including a first resistor $R_1$ between the first negative current feedback terminal $I_{fo1}$ and the current input terminal X, and connecting a second leg comprising a second resistor $R_2$ between the first negative current feedback terminal $I_{fo1}$ and a ground terminal.

In an aspect, connecting a second feedback path includes connecting a third resistor $R_3$ to the second negative current feedback terminal $I_{fo2}$, connecting a fourth resistor $R_4$ in series with the third resistor $R_3$, connecting a fifth resistor $R_5$ in series with the fourth resistor $R_4$, wherein the fifth resistor $R_5$ is connected to the input terminal x, connecting a first terminal of a first capacitor $C_1$ to the second negative current feedback terminal $I_{fo2}$ and connecting a second terminal of the first capacitor $C_1$ to the ground terminal, connecting a first terminal of a second capacitor $C_2$ to a junction between the third resistor $R_3$ and the fourth resistor $R_4$ and connecting a second terminal of the second capacitor $C_2$ to the ground terminal, and connecting a first terminal of a third capacitor $C_3$ to a junction between the fourth resistor $R_3$ and the fifth resistor $R_4$ and connecting a first second of a third capacitor $C_3$ to the ground terminal.

In an aspect, the method includes selecting the resistance of the first resistor $R_1$ and the resistance of the second resistor $R_2$ such that a condition of oscillation CO of the output current is met, subject to the calculation given by:

$$\left(1 + \frac{R_1}{R_2}\right) = 29.$$

In an aspect, the method includes selecting the resistance of the resistors in the second feedback path and the capacitance of the capacitors in the second feedback path to provide a desired frequency of oscillation $f_0$ of the output current wherein:

$$f_o = \frac{\sqrt{6}}{2\pi RC},$$

where $R=R_3=R_4=R_5$ and $C=C_1=C_2=C_3$.

In an aspect, the method includes selecting the resistance of $R_1$ to be about 32 kΩ, the resistance of $R_2$ to be about 1 kΩ, the resistance of R to be about 2 kΩ and the capacitance of C to be about 10 nF.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A current mode sinusoidal oscillator, comprising:
   a current amplifier having a current input terminal X, a first negative current feedback terminal $I_{fo1}$, a second negative current feedback terminal $I_{fo2}$, a positive current output terminal $I_{op}$ and a negative current output terminal $I_{on}$;
   a first feedback path connected between the first negative current feedback terminal $I_{fo1}$ and the input terminal X, wherein the first feedback path is configured to transmit a portion of a current at the first negative current feedback terminal $I_{fo1}$ to the current input terminal X;
   a second feedback path connected between the second negative current feedback terminal $I_{fo2}$ and the input terminal X, wherein the second feedback path is a three stage phase lag network configured to shift the phase of the current in the second feedback path by a negative 180 degrees with respect to the input current at a frequency of oscillation; and
   a load connected between the positive current output terminal $I_{op}$ and the negative current output terminal $I_{on}$, wherein an output current through the load is sinusoidal.

2. The current mode sinusoidal oscillator of claim 1, wherein the first feedback path comprises:
   a first leg including a first resistor $R_1$ connected between the first negative current feedback terminal $I_{fo1}$ and the current input terminal X, and
   a second leg comprising a second resistor $R_2$ connected between the first negative current feedback terminal $I_{fo1}$ and a ground terminal.

3. The current mode sinusoidal oscillator of claim 2, wherein the second feedback path comprises:

a third resistor $R_3$ connected to the second negative current feedback terminal $I_{fo2}$;

a fourth resistor $R_4$ connected in series with the third resistor $R_3$;

a fifth resistor $R_5$ connected in series with the fourth resistor $R_4$, wherein the fifth resistor $R_5$ is connected to the input terminal X;

a first capacitor $C_1$ having a first terminal connected to the second negative current feedback terminal $I_{fo2}$ and a second terminal connected to the ground terminal;

a second capacitor $C_2$ having a first terminal connected to a junction between the third resistor $R_3$ and the fourth resistor $R_4$ and having a second terminal connected to the ground terminal; and a third capacitor $C_3$ having a first terminal connected to a junction between the fourth resistor $R_3$ and the fifth resistor $R_4$ and having a second terminal connected to the ground terminal.

4. The current mode sinusoidal oscillator of claim 3, wherein a condition of oscillation (CO) of the output current is given by:

$$\left(1 + \frac{R_1}{R_2}\right) = 29.$$

5. The current mode sinusoidal oscillator of claim 3, wherein the frequency of oscillation $f_0$ of the output current is given by:

$$f_o = \frac{\sqrt{6}}{2\pi RC}$$

where $R=R_3=R_4=R_5$ and $C=C_1=C_2=C_3$.

6. The current mode sinusoidal oscillator of claim 5, wherein the resistor $R_1$ is about 32 k$\Omega$, the resistor $R_2$ is about 1 k$\Omega$, R is about 2 k$\Omega$ and C is about 10 nF, R is about 2 K$\Omega$ and C is about 10 nF.

7. The current mode sinusoidal oscillator of claim 1, wherein the load is a biomedical stimulation device selected from a group comprising a nerve stimulator, an electrode stimulator, a defibrillator, a deep brain stimulator and a muscle stimulator.

8. A current driver for biomedical stimulation, comprising:

a DC current source;

a switch connected to the DC current source, wherein the switch is configured to one of connect and disconnect the DC current;

a current amplifier having a current input terminal x connected to the switch, a first negative current feedback terminal $I_{fo1}$, a second negative current feedback terminal $I_{fo2}$, a positive current output terminal $I_{op}$ and a negative current output terminal $I_{on}$;

a first feedback path connected between the negative current feedback terminal $I_{fo1}$ and the input terminal x, wherein the first feedback path is configured to transmit a portion of a current at the first negative current feedback terminal $I_{fo1}$ to the current input terminal X;

a second feedback path connected between the second negative current feedback terminal $I_{fo2}$ and the input terminal x, wherein the second feedback path is a three stage phase lag network configured to shift the phase of the current in the second feedback path by a negative 180 degrees at a frequency of oscillation with respect to the input current; and a biomedical load connected between the positive current output terminal $I_{op}$ and the negative current output terminal $I_{on}$, wherein an output current driven through the biomedical load is sinusoidal.

9. The current driver of claim 8, wherein the first feedback path comprises:

a first leg including a first resistor $R_1$ connected between the first negative current feedback terminal $I_{fo1}$ and the current input terminal x, and a second leg comprising a second resistor $R_2$ connected between the first negative current feedback terminal $I_{fo1}$ and a ground terminal.

10. The current driver of claim 9, wherein the second feedback path comprises:

a third resistor $R_3$ connected to the second negative current feedback terminal $I_{fo2}$;

a fourth resistor $R_4$ connected in series with the third resistor $R_3$;

a fifth resistor $R_5$ connected in series with the fourth resistor $R_4$, wherein the fifth resistor $R_5$ is connected to the input terminal X;

a first capacitor $C_1$ having a first terminal connected to the second negative current feedback terminal $I_{fo2}$ and having a second terminal connected to the ground terminal;

a second capacitor $C_2$ having a first terminal connected to a junction between the third resistor $R_3$ and the fourth resistor $R_4$ and having a second terminal connected to the ground terminal; and a third capacitor $C_3$ having a first terminal connected to a junction between the fourth resistor $R_3$ and the fifth resistor $R_4$ and having a second terminal connected to the ground terminal.

11. The current driver of claim 10, wherein a condition of oscillation CO of the output current is given by:

$$\left(1 + \frac{R_1}{R_2}\right) = 29.$$

12. The current driver of claim 11, wherein the frequency of oscillation $f_0$ of the output current is given by:

$$f_o = \frac{\sqrt{6}}{2\pi RC}$$

where $R=R_3=R_4=R_5$ and $C=C_1=C_2=C_3$.

13. The current driver of claim 11, wherein the resistor $R_1$ is about 32 k$\Omega$, the resistor $R_2$ is about 1 k$\Omega$, R is about 2 k$\Omega$ and C is about 10 nF.

14. The current driver of claim 8, wherein the biomedical load is a biomedical stimulator selected from a group comprising a nerve stimulator, an electrode stimulator, a defibrillator, a deep brain stimulator and a muscle stimulator.

15. A method for providing biomedical stimulation, comprising:

connecting a DC current source to an input terminal of a current mode sinusoidal oscillator;

switching, by a switch connected to the DC current source, the DC current source ON;

wherein the current mode sinusoidal oscillator includes a current amplifier having a current input terminal X connected to the switch, a first negative current feedback terminal $I_{fo1}$, a second negative current feedback terminal $I_{fo2}$, a positive current output terminal $I_{op}$ and a negative current output terminal $I_{on}$;

connecting a first feedback path between the first negative current feedback terminal $I_{fo1}$ and the input terminal X, and transmitting a portion of a current at the first negative current feedback terminal $I_{fo1}$ to the current input terminal X;

connecting a second feedback path between the second negative current feedback terminal $I_{fo2}$ and the input terminal X, wherein the second feedback path is a three stage phase lag network configured to shift the phase of the current in the second feedback path by a negative 180 degrees with respect to the input current at a frequency of oscillation;

connecting a biomedical load between the positive current output terminal $I_{op}$ and the negative current output terminal $I_{on}$; and driving a sinusoidal output current through the biomedical load.

16. The method of claim 15, wherein connecting the first feedback path comprises:

connecting a first leg including a first resistor $R_1$ between the first negative current feedback terminal $I_{fo1}$ and the current input terminal X, and connecting a second leg comprising a second resistor $R_2$ between the first negative current feedback terminal $I_{fo1}$ and a ground terminal.

17. The method of claim 16, wherein connecting a second feedback path comprises:

connecting a third resistor $R_3$ to the second negative current feedback terminal $I_{fo2}$;

connecting a fourth resistor $R_4$ in series with the third resistor $R_3$;

connecting a fifth resistor $R_5$ in series with the fourth resistor $R_4$, wherein the fifth resistor $R_5$ is connected to the input terminal X;

connecting a first terminal of a first capacitor $C_1$ to the second negative current feedback terminal $I_{fo2}$ and connecting a second terminal of the first capacitor $C_1$ to the ground terminal;

connecting a first terminal of a second capacitor $C_2$ to a junction between the third resistor $R_3$ and the fourth resistor $R_4$ and connecting a second terminal of the second capacitor $C_2$ to the ground terminal; and connecting a first terminal of a third capacitor $C_3$ to a junction between the fourth resistor $R_3$ and the fifth resistor $R_4$ and connecting a first second of a third capacitor $C_3$ to the ground terminal.

18. The method of claim 17, further comprising:

selecting the resistance of the first resistor $R_1$ and the resistance of the second resistor $R_2$ such that a condition of oscillation CO of the output current is met, subject to the calculation given by:

$$\left(1 + \frac{R_1}{R_2}\right) = 29.$$

19. The method of claim 18, further comprising:

selecting the resistance of the resistors in the second feedback path and the capacitance of the capacitors in the second feedback path to provide a desired frequency of oscillation $f_0$ of the output current wherein:

$$f_o = \frac{\sqrt{6}}{2\pi RC}$$

where $R=R_3=R_4=R_5$ and $C=C_1=C_2=C_3$.

20. The method of claim 19, further comprising:

selecting the resistance of $R_1$ to be about 32 k$\Omega$, the resistance of $R_2$ to be about 1 k$\Omega$, the resistance of R to be about 2 k$\Omega$ and the capacitance of C to be about 10 nF.

* * * * *